United States Patent
Rand

(10) Patent No.: US 7,185,648 B1
(45) Date of Patent: Mar. 6, 2007

(54) MEDICAMENT DISPENSER

(76) Inventor: Paul Kenneth Rand, GlaxoSmithKline Five Moore Dr., P.O. Box 13398, Research Triangle Park, NC (US) 27709

(*) Notice: Subject to any disclaimer, the term of this patent is extended or adjusted under 35 U.S.C. 154(b) by 145 days.

(21) Appl. No.: 10/110,957

(22) PCT Filed: Sep. 28, 2000

(86) PCT No.: PCT/EP00/09641

§ 371 (c)(1),
(2), (4) Date: Apr. 18, 2002

(87) PCT Pub. No.: WO01/28608

PCT Pub. Date: Apr. 26, 2001

(30) Foreign Application Priority Data

Oct. 21, 1999 (GB) .................... 9924808

(51) Int. Cl.
A61M 11/00 (2006.01)
A61M 15/00 (2006.01)
B67D 5/64 (2006.01)
B01F 11/00 (2006.01)
B05B 1/08 (2006.01)

(52) U.S. Cl. ............. 128/200.23; 128/203.15; 222/160; 239/102.2; 366/117

(58) Field of Classification Search ................
128/200.11–200.14, 200.16, 200.17, 200.18,
128/200.21, 200.22, 200.23, 203.12, 203.14,
128/203.15, 203.19, 203.21–203.24, 203.28,
128/204.13, 204.14; 366/117, 118, 127;
222/160–162, 166, 167, 196, 233, 235, 402.1,
222/402.25; 239/102.2, 3, 690, 690.1, 650,
239/654, 676, 683, 142, 329, 322
See application file for complete search history.

(56) References Cited

U.S. PATENT DOCUMENTS

| 2,877,994 | A | | 3/1959 | Jones et al. |
| 3,042,310 | A | * | 7/1962 | Reinhold et al. ........... 239/142 |
| 3,384,354 | A | * | 5/1968 | Albrecht et al. ........... 366/118 |
| 3,456,644 | A | | 7/1969 | Thiel |
| 3,565,070 | A | | 2/1971 | Hanson et al. |
| 3,598,294 | A | | 8/1971 | Hedrick et al. |
| 3,636,949 | A | | 1/1972 | Kropp |
| 3,789,843 | A | | 2/1974 | Armstrong et al. |
| 3,863,903 | A | * | 2/1975 | Brehmer et al. ........... 366/274 |
| 3,971,377 | A | | 7/1976 | Damani |
| 4,061,315 | A | | 12/1977 | Eitzen et al. |
| 4,184,778 | A | | 1/1980 | Terrels |
| 4,240,418 | A | | 12/1980 | Rosskamp et al. |
| 4,259,021 | A | * | 3/1981 | Goudy, Jr. ................. 366/118 |
| 4,502,342 | A | | 3/1985 | Kraft et al. |

(Continued)

FOREIGN PATENT DOCUMENTS

DE  31 15 568  4/1982

(Continued)

OTHER PUBLICATIONS

Patent Abstracts of Japan, vol. 011, No. 054 (M-563), Feb. 19, 1987 & JP 61 217431 A (Kobe Steel LTD), Sep. 27, 1986 Abstract.
European Search Report for Application No. 00966101.8 dated Dec. 7, 2005.

Primary Examiner—Teena K. Mitchell
(74) Attorney, Agent, or Firm—Robert J. Smith

(57) ABSTRACT

A medicament dispenser including a medicament container having a dispensing outlet; an agitator for agitating the contents; and a driver for driving the agitator independent of any container movement. The medicament container may be a metered dose inhaler or delivering a suitable inhalable medicament.

33 Claims, 4 Drawing Sheets

U.S. PATENT DOCUMENTS

| | | | | |
|---|---|---|---|---|
| 4,518,103 A | * | 5/1985 | Lim et al. | 222/135 |
| 4,612,291 A | | 9/1986 | Dawes | |
| 4,648,393 A | | 3/1987 | Landis et al. | |
| 4,759,635 A | | 7/1988 | MacMichael et al. | |
| 4,808,006 A | * | 2/1989 | Kaufeler | 366/322 |
| 4,858,759 A | * | 8/1989 | Mauthe et al. | 206/221 |
| 5,027,808 A | | 7/1991 | Rich et al. | |
| 5,071,040 A | * | 12/1991 | Laptewicz, Jr. | 222/235 |
| 5,221,025 A | | 6/1993 | Privas | |
| 5,347,998 A | | 9/1994 | Hodson et al. | |
| 5,352,036 A | | 10/1994 | Haber et al. | |
| 5,397,178 A | * | 3/1995 | Konietzko | 366/197 |
| 5,449,493 A | | 9/1995 | Rokugawa et al. | |
| 5,451,105 A | | 9/1995 | Koering | |
| 5,487,378 A | * | 1/1996 | Robertson et al. | 128/200.16 |
| 5,608,693 A | | 3/1997 | Richards | |
| 5,622,166 A | | 4/1997 | Eisele et al. | |
| RE35,552 E | | 7/1997 | Lankinen | |
| 5,727,541 A | * | 3/1998 | Rowland | 128/200.14 |
| 5,743,250 A | | 4/1998 | Gonda et al. | |
| 5,842,786 A | * | 12/1998 | Solomon | 366/139 |
| 5,879,081 A | * | 3/1999 | Chordia | 366/249 |
| 5,894,841 A | * | 4/1999 | Voges | 128/203.12 |
| 6,116,234 A | | 9/2000 | Genova et al. | |
| 6,119,688 A | | 9/2000 | Whaley et al. | |
| 6,293,693 B1 | * | 9/2001 | Rodgers et al. | 366/189 |
| 6,308,704 B1 | | 10/2001 | Wennerberg | |
| 6,378,518 B1 | * | 4/2002 | Miekka et al. | 128/203.15 |
| 6,387,077 B1 | | 5/2002 | Klibanov et al. | |
| 6,394,086 B1 | * | 5/2002 | Barnes et al. | 128/203.15 |
| 6,454,193 B1 | * | 9/2002 | Busick et al. | 239/690 |
| 6,474,563 B2 | * | 11/2002 | Pletcher et al. | 239/3 |
| 6,729,559 B2 | * | 5/2004 | Zanma et al. | 239/225.1 |
| 6,743,413 B1 | * | 6/2004 | Schultz et al. | 424/45 |
| 2003/0056789 A1 | * | 3/2003 | Takano et al. | 128/203.12 |

FOREIGN PATENT DOCUMENTS

| | | | |
|---|---|---|---|
| GB | 997 088 A | | 6/1965 |
| GB | 2 129 322 | | 5/1984 |
| GB | 2262452 | * | 6/1993 |
| WO | 95/30607 | | 11/1995 |
| WO | WO 97/44080 | * | 11/1997 |
| WO | 99 47195 A | | 9/1999 |
| WO | 00/44423 | | 8/2000 |

* cited by examiner

MEDICAMENT DISPENSER

The instant application is filed under 35 U.S.C. § 371 as the United States National Phase Application of International Application No. PCT/EP00/09641 filed 28 Sep. 2000 claiming priority from GB 9924808.0 filed 21 Oct. 1999.

TECHNICAL FIELD

This invention relates to a medicament dispenser including an agitator for agitating the medicament contents thereof. The dispenser is particularly suitable for use as an inhalation device.

BACKGROUND TO THE INVENTION

Known medicament dispensers comprise a medicament container having a dispensing outlet for dispensing of the medicament therefrom. Such medicament dispensers often require the patient to agitate the contents thereof prior to dispensing to ensure ready and uniform dispensing of the medicament. The agitation involves a manual shaking action.

Agitation is particularly required where the dispenser comprises medicament as a suspension in a propellant formulation. A well-known example of this type is the metered dose inhaler for dispensing of respiratory medicament which comprises an aerosol container having a dispensing valve. The medicament is comprised within the aerosol container in the form of a suspension comprising propellant and optionally other additives such as solvents or surfactants. Such suspensions have a tendency to settle out, sediment or cream. A pre-dispensing agitation step is necessary to re-establish a uniform suspension so that uniform dispensing of medicament may be achieved.

Agitation can also be required where the medicament is in powder form. It is known that powders can tend to settle out, agglomerate or even cake on storage. The agitation therefore performs the function of breaking up any agglomerates or cakes that may have formed, and thereby ensures that the powder is readily dispensable.

Various suggestions have been made to enhance manual shaking action to maximise the effect of agitation.

PCT Patent Application No. WO95/30607 describes a metered dose dispensing valve including a movable agitator in the metering chamber. Manual shaking of the valve causes movement of the agitator therein which is stated to assist mixing of the drug suspension in the metering chamber.

PCT Patent Application No. WO96/08284 describes an inhalation device for dispensing powder form medicament including a movable weight which is configured to strike an anvil upon manual shaking of the device. The striking action causes a jolt which acts such as to assist transfer of the powder from a reservoir container to a metering recess formed in a dosing member.

Whilst manual shaking is a generally effective means for providing agitation it is sometimes inconvenient for the patient. In social situations, the patient often wishes to administer their medicament discretely and without drawing attention to themselves. Manual shaking of the dispenser is difficult to perform in a discrete fashion. This can lead to patient embarrassment. There is also always the possibility that the patient forgets to shake the dispenser, or does so inadequately, thereby affecting the medicament dose deliverable.

The Applicants have now developed a medicament dispenser which requires little or no manual shaking. The dispenser comprises a medicament container and an agitator for agitating the contents of the medicament container. A drive is provided for driving the agitator independently of any movement of the container. The dispenser therefore provides for agitation of the medicament container and contents thereof without requiring shaking by the patient.

SUMMARY OF INVENTION

According to one aspect of the present invention there is provided a medicament dispenser comprising a medicament container having a dispensing outlet; an agitator for agitating the contents of the container; and a driver for driving the agitator independently of any movement of the container, wherein the driver comprises an energy store for storing energy which energy is releasable to drive the agitator.

Preferably, the agitator comprises a movable element within said container. More preferably, the movable element is freely movable within the container.

In one aspect, the movable element is magnetically coupled to the driver. Preferably, either or both of the movable element or the driver comprises magnetic material or material which is magnetically inductive, that is to say material into which magnetism can be induced. The material may be permanently or non-permanently magnetisable.

In another aspect, the movable element is mechanically coupled to the driver.

In a preferred aspect, the container includes a rim defining an access hole, the movable element comprises a flexible sheath protruding through said access hole, and the driver comprises a rod insertable within said flexible sheath for agitation thereof. Preferably, the flexible sheath is in sealing contact with the rim.

In another aspect, the movable element is pneumatically drivable.

In another aspect, the movable element is hydraulically drivable.

In another aspect, the movable element is electrically drivable. Preferably, the movable element comprises a multi-component strip or wire which is deformable in response to electrical current flow.

Suitable multi-component strips typically comprise a plurality of layers of material, each material having a different coefficient of thermal expansion. Preferred examples of multi-component strips include strips comprising multiple layers of different metals (e.g. bimetallic strips) and strips comprising at least one piezoelectric or piezoresistive material. Suitable piezoelectric materials include piezoelectric ceramics, such as compounds of lead zirconate and lead titanate, and piezoelectric crystals which are generally polycrystalline ferroelectric materials with the perovskite structure.

Suitable multi-component wires typically comprise alloys of two or more metals wherein one or more of the metals undergoes a temperature induced phase change in response to electrical current flow. Preferred examples of multi-component wires include those comprised of alloys of titanium and nickel which contract when electric current is applied.

Preferably, the movable element is shaped to create turbulence within the container when agitated.

In one aspect, the agitator creates regions of pressure difference within the container. Preferably, the agitator comprises a piston mechanism within the container. More preferably, the piston mechanism is mechanically drivable by the driver. Most preferably, the drive comprises a plunger for moving the piston.

In another aspect, the agitator provides wave energy to the interior of the container. Preferably, the agitator is an acoustic wave energy generator or a resonant wave energy generator.

In one aspect, the driver is associable with the container. The driver may be external to, or internal to, the container and may be permanently or reversibly attached to the container.

In another aspect, the medicament dispenser additionally comprises a housing. Preferably the driver is associable with the housing. The driver may be external to, or internal to, the housing and may be permanently or reversibly attached to the housing.

In one aspect, the energy store comprises a biasable resilient member. Preferably, the biasable resilient member is a spring.

In another aspect, the energy store comprises a clockwork mechanism.

In another aspect, the energy store comprises a battery.

Preferably, the driver is responsive to a patient-actuable trigger. The trigger may comprise a button, switch or lever arrangement. More preferably, the trigger comprises a sensor which senses the breath of a patient.

In one aspect, the sensor comprises a breath-movable element which is movable in response to the breath of a patient. Preferably, the breath-movable element is selected from the group consisting of a vane, a sail, a piston and an impeller.

In another aspect, the sensor comprises a pressure sensor for sensing the pressure profile associated with the breath of a patient.

In another aspect, the sensor comprises an airflow sensor for sensing the airflow profile associated with the breath of a patient.

In another aspect, the sensor comprises a temperature sensor for sensing the temperature profile associated with the breath of a patient.

In another aspect, the sensor comprises a moisture sensor for sensing the moisture profile associated with the breath of a patient.

In another aspect, the sensor comprises a gas sensor for sensing the oxygen or carbon dioxide profile associated with the breath of a patient.

Preferably, dispensing from the dispensing outlet is responsive to a second patient-actuable trigger. More preferably, the patient-actuable triggers are coupled such that agitation and dispensing occurs in a sequential fashion.

In one preferred aspect, the container is an aerosol container, preferably comprising a metering valve at the dispensing outlet. Preferably, the aerosol container comprises a suspension of a medicament in a propellant.

The propellant preferably comprises liquefied HFA134a, HFA-227 or carbon dioxide.

The medicament is preferably selected from the group consisting of albuterol, salmeterol, fluticasone propionate, beclomethasone dipropionate, salts or solvates thereof and any mixtures thereof.

BRIEF DESCRIPTION OF THE INVENTION

The invention will now be described further with reference to the accompanying drawings in which.

DETAILED DESCRIPTION OF THE INVENTION

Figure 1:
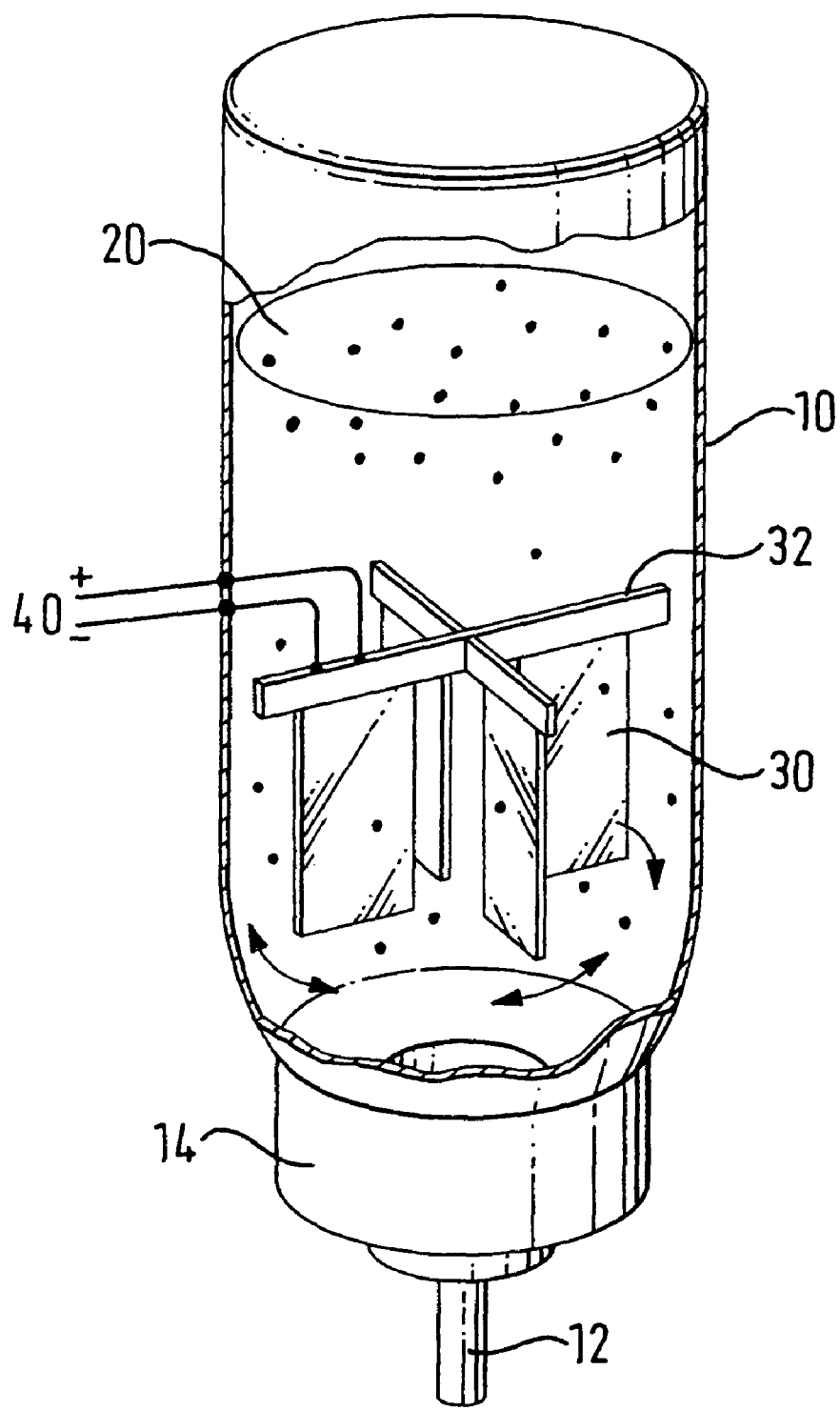
FIG. 1 is a cut-away perspective view of a first medicament dispenser in accord with the present invention.

FIG. 1. shows a medicament dispenser suitable for use in a metered dose inhaler (MDI) for delivery of inhalable medicament. The dispenser comprises an aerosol can 10 having a dispenser outlet in the form of a metering valve 12. The valve gasket 14 is fixedly attached (typically by crimping) to the aerosol can body 10. The can 10 comprises a suspension 20 of medicament in a propellant.

Within the can 10 there are provided four vibratable flippers 30 mounted on cross-mounting 32. Each vibratable flipper 30 is comprised of a bimetallic strip which flexes on application of electrical current. In alternative embodiments, the flippers may also comprise piezoelectric materials. The cross-mounting 32, and hence each flipper 30, is connected to external electric power source 40 which may be in the form of a battery or a capacitor. On application of electric power the flippers 30 vibrate thereby resulting in agitation of the suspension 20.

Figure 2:
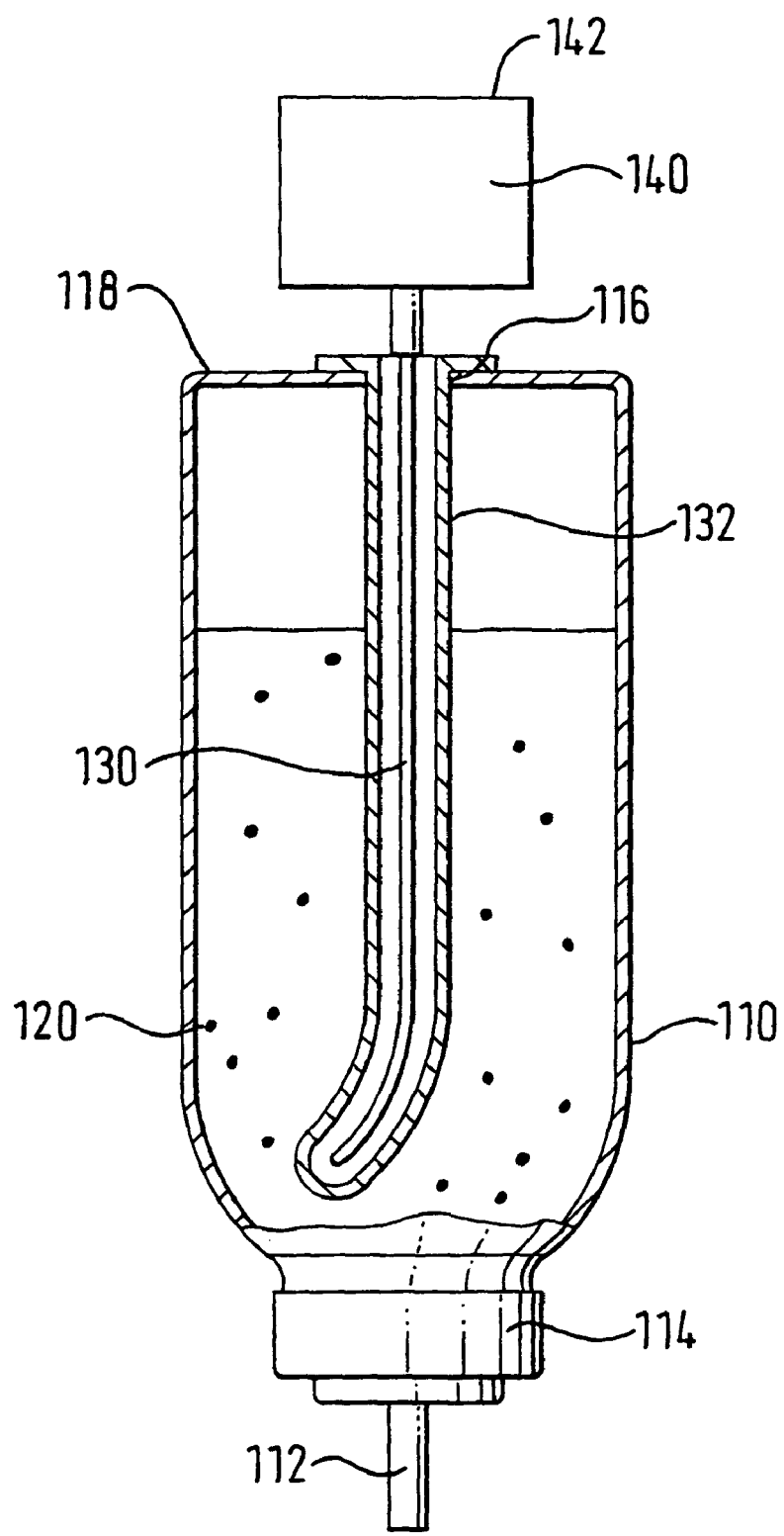
FIG. 2 is a sectional view of a second medicament dispenser in accord with the present invention.

FIG. 2. also shows a medicament dispenser suitable for use in a metered dose inhaler (MDI) for delivery of inhalable medicament. The dispenser comprises an aerosol can 110 having a dispenser outlet in the form of a metering valve 112. The valve gasket 114 is fixedly attached (typically by crimping) to the aerosol can body 110. The can 110 comprises a suspension 120 of medicament in a propellant.

It may be seen that an access hole 116 is provided in the base 118 of the aerosol can 110 for receipt of flexible elongate sheath 132. The sheath 132 typically comprises a latex, rubber or elastomeric material and may be seen to protrude well into the interior of the can 110. Within the sheath 132 there is provided drive rod 130 which comprises a resiliently flexible material. The drive rod 130 connects to drive motor 140 which may for example, be an electric or clockwork motor. The drive motor 140 may in embodiments be configured to provide oscillatory or rotatory drive motion to the drive rod 130. On application of the drive energy the drive rod 130 moves within the sheath 132 thereby resulting in agitation of the suspension 120.

In an alternative embodiment, the electric or clockwork drive motor 140 is replaced by a mechanical push-drive which is capable of translating a push motion (e.g. at the top 142 of the drive) into a rotatory drive motion. Such a push-drive could incorporate a suitably configured gear train or worm and helix drive mechanism. In known metered dose inhalers wherein the can 110 sits within an actuator housing, the dispensing action typically requires the user to push down on the base 118 of the can 110 such that the valve 112 is released. It may be appreciated that the use of the push-drive will facilitate a agitation-dispensing sequence in which a first user pushing action on the push-drive results in agitation of the suspension 120 and a second user pushing action (which may be a continuation of the first) results in dispensing of the suspension 120.

Figure 3:
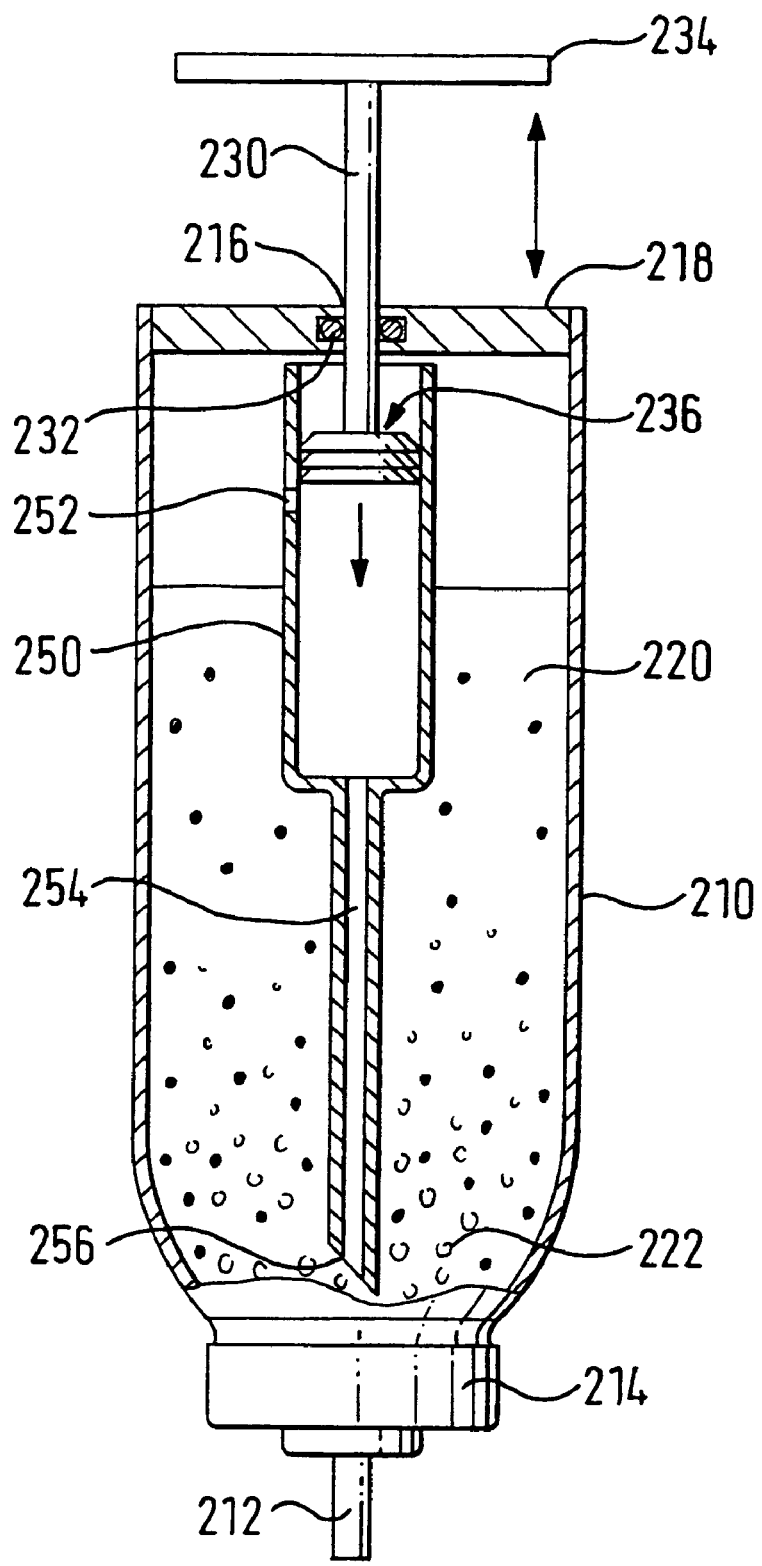
FIG. 3 is a sectional view of a third medicament dispenser in accord with the present invention.
Figure 4A:
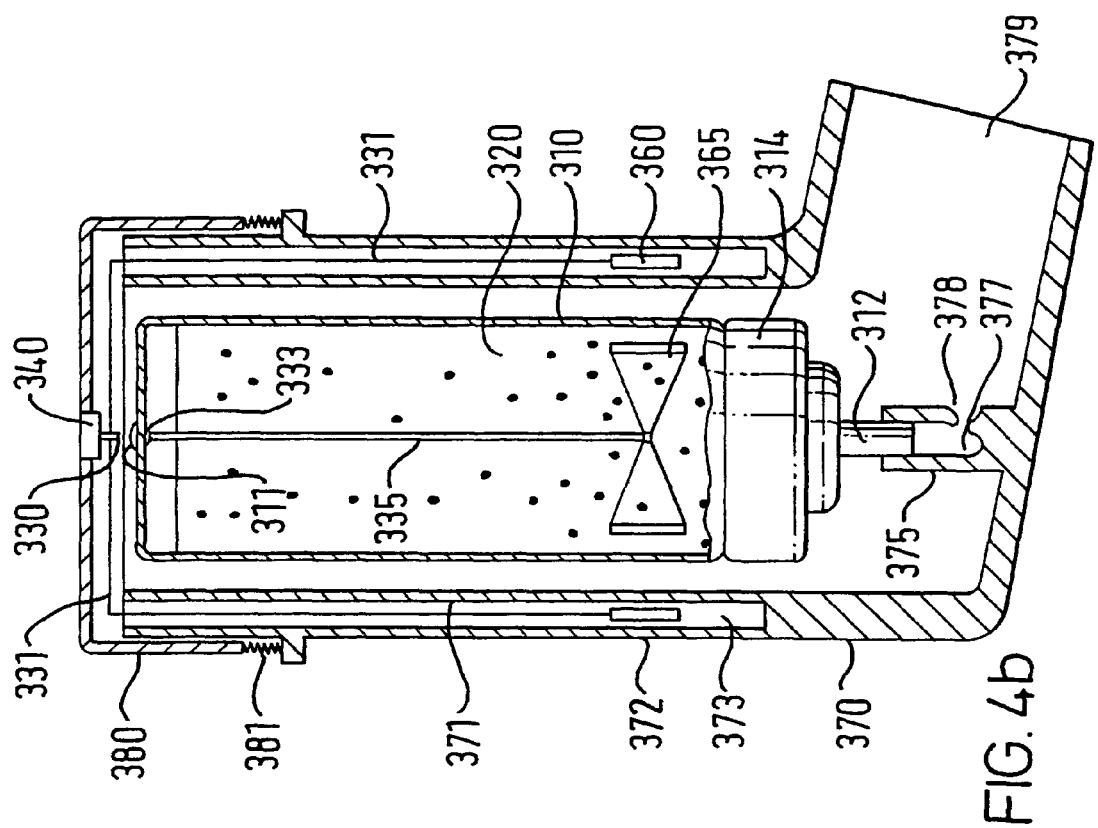
FIGS. 4a and 4b are sectional views of a fourth medicament dispenser in accord with the present invention.
Figure 4B:
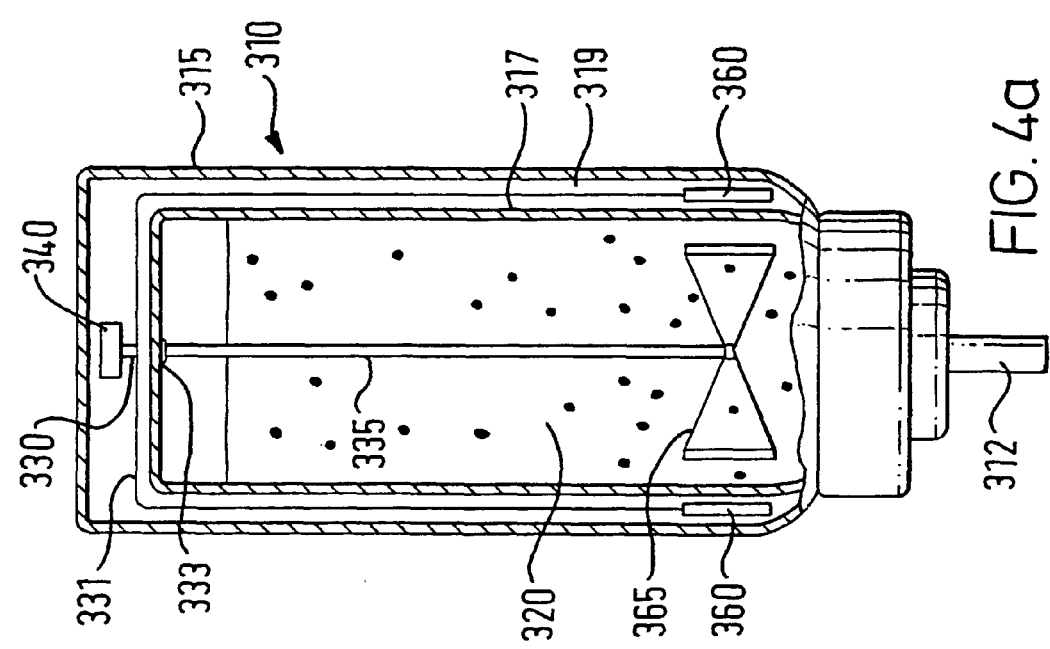

FIG. 3. shows a further medicament dispenser suitable for use in a metered dose inhaler (MDI) for delivery of inhalable medicament. The dispenser comprises an aerosol can 210 having a dispenser outlet in the form of a metering valve 212. The valve gasket 214 is fixedly attached (typically by crimping) to the aerosol can body 210. The can 210 comprises a suspension 220 of medicament in a propellant.

It may be seen that an access hole 216 is provided in the base 218 of the aerosol can 210 for receipt of dynamic seal 232. The dynamic seal 232 typically comprises a rigid elastomeric material and may be seen to form a liner to the access hole 216. Protruding through the dynamic seal 232 there is provided piston drive shaft 230. Piston drive shaft 230 has a shaped plunger head 234 which may in embodiments, be connected to a drive motor (not shown) such as an electric or clockwork motor. Piston 236 is received by cylinder 250 within which it is drivable. It may be seen that cylinder 250 includes entry hole 252 and narrows at its lower end to form tube 254 having exit hole 256.

Agitation of the suspension 220 within the can 210 is achieved by a driving movement of the piston 236 within the cylinder 250. In more detail, it can be seen that when the piston 236 is in the withdrawn position (as shown in FIG. 3) gas may enter cylinder 250 through entry hole 252. As the piston 236 is moved downwards the gas is initially trapped in the cylinder 250, then pushed through tube 254 and finally expelled through exit hole 256. Expulsion of the gas results in formation of bubbles 222 and flow agitation in the suspension 220.

FIG. 4*a* shows a medicament dispenser suitable for use in a metered dose inhaler for delivery of inhalable medicament. The dispenser comprises an aerosol canister 310 having a dispenser outlet 312 in the form of a metering valve. The canister 310 has an external 315 and internal 317 wall with cavity 319 therebetween. A suspension 320 of a medicament in a propellant is contained within internal wall 317 of the canister. A magnetic impeller 365 is located within canister 310 and is free to rotate around axis 333 on shaft 335.

Within cavity 319 there is provided an electric or clockwork motor 340 which connects via drive shaft 330 to magnet 360. The electric motor may be powered by any suitable means, such as a battery (not shown). The magnet 360 may be rotated or oscillated on arm 331, connecting to drive shaft 330, around internal wall 317 when powered by the motor 340. It may be appreciated that rotation or oscillation of arm 331 and of magnet 360 will result in rotation or oscillation of magnetic impeller 365.

Agitation of the suspension 320 within the aerosol canister 310 is achievable by the following steps. The motor 340 is actuated by means of a pressure switch (not shown) to rotate drive shaft 330 and arm 331, thereby rotating magnet 360 within cavity 319. The magnet 360 on arm 331 acts magnetically on the magnetic impeller 365 within the can 310 such that the impeller 365 is also rotated. Rotation of the magnetic impeller 365 agitates the suspension 320.

FIG. 4*b* shows a variation of the dispenser of FIG. 4*a*. In the metered dose inhalation device of FIG. 4*b* an aerosol canister 310 is located within housing 370 such that dispenser outlet 312 is positioned within passage 377 of support 375. A second passage 378 is provided within support 375 and is directed towards the interior of outlet 379.

Aerosol canister 310 contains a suspension 320 of a medicament in a propellant. Magnetic impeller 365 is located within canister 310 and is free to rotate on shaft 335 about axis 333. Detachable cap 380 encloses aerosol canister 310 within housing 370. The cylindrical housing 370 divides into an internal 371 and external 372 wall with cavity 373 therebetween. In the position shown, magnet 360 is suspended from arm 331, connected to drive shaft 330, and is free to rotate or oscillate within the cavity 373 when powered by electric or clockwise motor 340. It will be appreciated that rotation of magnet 360 leads to rotation of magnetic impeller 365 and thus agitation of suspension 320.

To use the device, cap 380 is compressed thereby activating a pressure switch (not shown) of motor 340 leading to rotation of magnet 360 within cavity 373. Magnetic impeller 365 is thus rotated within canister 310 and agitates suspension 320. Further compression of cap 380 pushes drive shaft 330 against canister block 311, stopping rotation of the drive shaft and moving canister 310 relative to valve member 312. This action opens the valve and a dose of medicament contained within the aerosol canister is dispensed through passage 378 into outlet 379 to be inhaled by the patient. On removal of the pressure, resilient material 381 returns cap 380 to its resting position.

It may be appreciated that any of the parts of the dispenser which contact the medicament suspension may be coated with materials such as fluoropolymer materials which reduce the tendency of medicament to adhere thereto. Any movable parts may also have coatings applied thereto which enhance their desired movement characteristics. Frictional coatings may therefore be applied to enhance frictional contact and lubricants used to reduce frictional contact as necessary.

The medicament dispenser of the invention is suitable for dispensing medicament, particularly for the treatment of respiratory disorders such as asthma and chronic obstructive pulmonary disease. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. s the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); α4 integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant. Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g. as the fumarate salt) in combination with an antiinflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. A metered dose inhaler comprising an aerosol container which:
   contains a suspension of a medicament in a propellant, and
   has a dispensing outlet and a metering valve at the dispensing outlet;
   an agitator for agitating the contents of the container, the agitator comprising a movable element located within the container; and
   a driver for driving said agitator independently of any movement of the container.

2. A metered dose inhaler according to claim 1, wherein the movable element is freely movable within the container.

3. A metered dose inhaler according to claim 2, wherein the movable element is mechanically coupled to the driver.

4. A metered dose inhaler according to claim 2, wherein the container includes a rim defining an access hole, the movable element comprises a flexible sheath protruding through said access hole, and the driver comprises a rod insertable within said flexible sheath for agitation thereof.

5. A metered dose inhaler according to claim 4, wherein the flexible sheath is in sealing contact with the rim.

6. A metered dose inhaler according to claim 1, wherein the movable element is magnetically coupled to the driver.

7. A metered dose inhaler according to claim 6, wherein either or both of the movable element or the driver comprises magnetic material or material which is magnetically inductive.

8. A metered dose inhaler medicament dispenser according to claim 1, wherein the movable element is pneumatically drivable.

9. A metered dose inhaler according to claim 1, wherein the movable element is hydraulically drivable.

10. A metered dose inhaler according to claim 1, wherein the movable element is electrically drivable.

11. A metered dose inhaler according to claim 10, wherein the movable element comprises a multi-component strip or wire which is deformable in response to electrical current flow.

12. A metered dose inhaler according to claim 11, wherein said multi-component strip or wire comprises multiple layers of different metals.

13. A metered dose inhaler according to claim 12, wherein the multi-component strip comprises a bimetallic strip.

14. A metered dose inhaler according to claim 11, wherein the multi-component strip comprises at least one piezoelectric or piezoresistive material.

15. A metered dose inhaler according to claim 14, wherein said multi-component wire comprises a nickel-titanium alloy.

16. A metered dose inhaler according to claim 1, wherein the movable element is shaped to create turbulence within the container when agitated.

17. A metered dose inhaler according to claim 1, wherein the agitator creates regions of pressure difference within the container.

18. A metered dose inhaler according to claim 17, wherein the agitator provides wave energy to the interior of the container.

19. A metered dose inhaler according to claim 18, wherein the agitator is an acoustic wave energy generator.

20. A metered dose inhaler according to claim 18, wherein the agitator is a resonant wave energy generator.

21. A metered dose inhaler according to claim 17, wherein the agitator comprises a piston mechanism within the container.

22. A metered dose inhaler according to claim 21, wherein the piston mechanism is mechanically drivable by the driver.

23. A metered dose inhaler according to claim 22, wherein the drive comprises a plunger for moving the piston.

24. A metered dose inhaler according to claim 1, wherein the driver is associable with the container.

25. A metered dose inhaler according to claim 1, additionally comprising a housing.

26. A metered dose inhaler according to claim 25, wherein the driver is associable with said housing.

27. A metered dose inhaler according to claim 1, wherein the driver comprises an energy store for storing energy which energy is releasable to drive the agitator.

28. A metered dose inhaler according to claim 27, wherein said energy store comprises a biasable resilient member.

29. A metered dose inhaler according to claim 28, wherein said biasable resilient member is a spring.

30. A metered dose inhaler according to claim 27, wherein the energy store comprises a clockwork mechanism.

31. A metered dose inhaler according to claim 27, wherein the energy store comprises a battery.

32. A metered dose inhaler according to claim 1, wherein the driver is responsive to a patient-actuable trigger.

33. A metered dose inhaler A medicament dispenser according to claim 1, wherein said propellant comprises liquefied HFA134a, HFA-227 or carbon dioxide.

* * * * *